United States Patent
Ishikawa et al.

(10) Patent No.: US 8,756,033 B2
(45) Date of Patent: Jun. 17, 2014

(54) ULTRASONIC DIAGNOSTIC IMAGING SYSTEM AND CONTROL METHOD THEREOF

(75) Inventors: Ryo Ishikawa, Kawasaki (JP); Akihiro Katayama, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 549 days.

(21) Appl. No.: 12/673,097

(22) PCT Filed: Aug. 13, 2008

(86) PCT No.: PCT/JP2008/064764
§ 371 (c)(1),
(2), (4) Date: Feb. 11, 2010

(87) PCT Pub. No.: WO2009/028354
PCT Pub. Date: Mar. 5, 2009

(65) Prior Publication Data
US 2011/0246129 A1 Oct. 6, 2011

(30) Foreign Application Priority Data
Aug. 31, 2007 (JP) ................................. 2007-226340

(51) Int. Cl.
*G01C 9/00* (2006.01)
(52) U.S. Cl.
USPC ....................................................... 702/150
(58) Field of Classification Search
USPC ....................................................... 702/150
See application file for complete search history.

(56) References Cited

U.S. PATENT DOCUMENTS

| 5,715,166 A | * | 2/1998 | Besl et al. | 700/182 |
| 6,425,865 B1 | * | 7/2002 | Salcudean et al. | 600/437 |
| 7,824,348 B2 | * | 11/2010 | Barthe et al. | 601/3 |
| 2003/0187345 A1 | | 10/2003 | Mochizuki | 600/407 |
| 2004/0019270 A1 | * | 1/2004 | Takeuchi | 600/407 |

FOREIGN PATENT DOCUMENTS

| EP | 1348377 | 7/2002 |
| JP | H01-025576 | 1/1989 |
| JP | 2004-000499 | 1/2004 |
| JP | 2007-050107 A | 3/2007 |
| WO | WO 2006/059668 A | 6/2006 |
| WO | WO 2006/092602 | 9/2006 |

OTHER PUBLICATIONS

Office Action issued Jul. 3 in counterpart Japanese Patent Application No. 2007-226340, with translation.

(Continued)

*Primary Examiner* — Aditya Bhat
(74) *Attorney, Agent, or Firm* — Fitzpatrick, Cella, Harper & Scinto

(57) ABSTRACT

An ultrasonic diagnostic imaging system not depending on an operator who operates the apparatus is provided. The system includes a measuring unit (coordinate calculation section 2034) that measures a relative position and a relative posture of the ultrasonic probe with respect to an examinee using image information on the examinee acquired by the ultrasonic probe, a control amount calculation unit (2035) that calculates an amount of control of the position and posture of the ultrasonic probe based on the measurement result of the measuring unit and at least one of a probe control mechanism that controls the position and posture of the ultrasonic probe using the amount of control calculated by the control amount calculation unit and a guiding information presentation unit that presents information for guiding movement of the position and posture of the ultrasonic probe using the amount of control calculated by the control amount calculation unit.

28 Claims, 11 Drawing Sheets

(56) References Cited

OTHER PUBLICATIONS

Office Action issued Mar. 21, 2012, issued in counterpart Japanese Patent Application No. 2007-226340, and translation.

Extended European Search Report dated Apr. 3, 2013, issued in counterpart European Patent Application No. 12195661.9.
Extended European Search Report dated Apr. 5, 2013, issued in counterpart European Patent Application No. 12195661.9.

* cited by examiner

SUPERIMPOSITION ated from received data. Even when irradiated onto the human body, ultrasound is safe without any particular side effects, and is therefore widely used for diagnostics of various diseases on the medical front lines.

ULTRASONIC DIAGNOSTIC IMAGING SYSTEM AND CONTROL METHOD THEREOF

This application is national phase of PCT Application No. PCT/JP2008/064764 filed Aug. 13, 2008, which in turn claims benefit of JP 2007-226340 filed Aug. 31, 2007.

TECHNICAL FIELD

The present invention relates to an ultrasonic diagnostic imaging system and a control method thereof.

BACKGROUND ART

An ultrasonic diagnostic imaging apparatus (echo) is a diagnostic apparatus that irradiate an examinee with ultrasound, receives ultrasound reflected inside the examinee using a probe and obtains image information from received data. Even when irradiated onto the human body, ultrasound is safe without any particular side effects, and is therefore widely used for diagnostics of various diseases on the medical front lines.

The ultrasound medical system disclosed in Japanese Patent Application Laid-Open No. 2004-499 discloses a medical system that combines a radiation system for radiological treatment with an ultrasonic diagnostic imaging apparatus. The ultrasonic diagnostic imaging apparatus provides positional information using the position of the radiation apparatus as the origin when providing the position of a tumor to be cured.

The ultrasound diagnostic apparatus is a simple diagnostic apparatus from the aspect that the ultrasound diagnostic apparatus can acquire image information by only pressing an ultrasonic probe on the human body. A doctor who operates the ultrasound diagnostic apparatus acquires an image by pressing the ultrasonic probe on a patient's body and moving the probe as appropriate. However, since there are many organs in the human body, obtaining image information on an organ to be diagnosed appropriately requires a certain degree of skill in moving the ultrasonic probe.

Japanese Patent Application Laid-Open No. H01-025576 describes a "scanner of ultrasonic probe." The position, posture and pressure at an end of an ultrasonic probe are measured and the ultrasonic probe is moved and controlled in such a way that the position, posture and pressure are kept constant.

The method of complementing the skill of the user regarding a scan technique, which is an operation technique, through such control is disclosed.

The above described method allows the state of the probe with respect to the surface of the human body to be kept adequately. However, keeping the ultrasonic probe in an appropriate state with respect to a region to be inspected in the examinee still requires the operator to have the corresponding skill and knowledge.

DISCLOSURE OF THE INVENTION

In view of the above described problems, it is an object of the present invention to provide an ultrasound diagnostic system and a control method thereof that enables image information on an examinee's tissue to be diagnosed to be appropriately obtained.

In order to solve the above described problems, one aspect of the present invention is an ultrasonic diagnostic imaging system provided with an ultrasonic probe and an image processing section that converts a signal generated when the ultrasonic probe receives ultrasound reflected from an examinee to image information, including a measuring unit that measures a relative position and a relative posture of the ultrasonic probe with respect to the examinee using image information on the examinee acquired by the ultrasonic probe, a control amount calculation unit that calculates an amount of control of the position and posture of the ultrasonic probe based on the measurement result of the measuring unit and at least one of a probe control mechanism that controls a position and posture of the ultrasonic probe using the amount of control calculated by the control amount calculation unit and a guiding information presentation unit that presents information for guiding movement of the position and posture of the ultrasonic probe using the amount of control calculated by the control amount calculation unit.

Furthermore, another aspect of the present invention is a control method for an ultrasonic diagnostic imaging system provided with an ultrasonic probe and an image processing section that converts a signal generated when the ultrasonic probe receives ultrasound reflected from an examinee to image information, measuring a relative position and relative posture of the ultrasonic probe with respect to the examinee using image information on the examinee acquired by the ultrasonic probe, calculating an amount of control of a position and posture of the ultrasonic probe based on the measurement result and at least one of controlling the position and posture of the ultrasonic probe using the calculated amount of control and presenting information for guiding movement of the position and posture of the ultrasonic probe using the amount of control calculated by the control amount calculation unit.

The present invention adopts a configuration capable of calculating an appropriate position and posture of an ultrasonic probe in an ultrasonic image diagnosis, and can thereby provide a system not depending on an operator who operates the apparatus.

Other features and advantages of the present invention will be apparent from the following description taken in conjunction with the accompanying drawings, in which like reference characters designate the same or similar parts throughout the figures thereof.

BEST MODES FOR CARRYING OUT THE INVENTION

Figure 1:
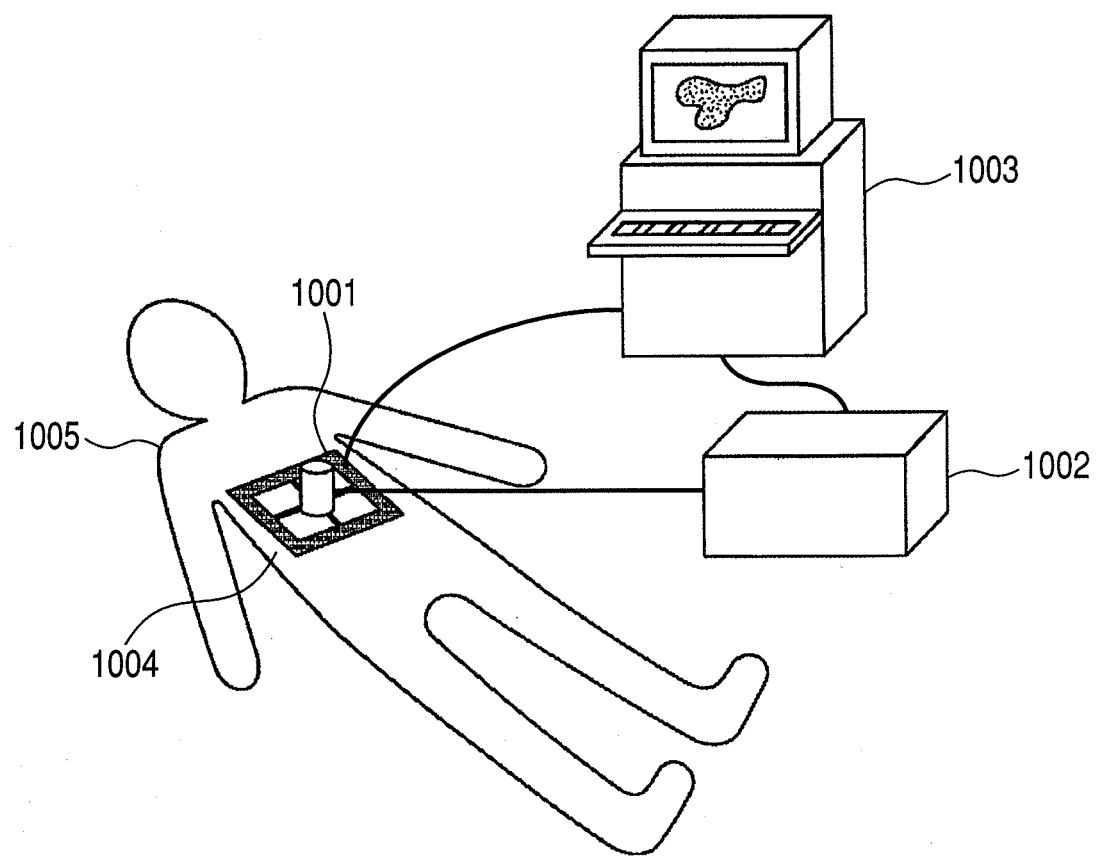
FIG. 1 illustrates a diagnostic method using an ultrasonic diagnostic imaging system according to the present invention.

Preferred embodiments of the present invention will now be described in detail in accordance with the accompanying drawings.

Hereinafter, embodiments of an ultrasonic diagnostic imaging apparatus and a control method thereof according to the present invention will be described in detail according to the accompanying drawings. However, the scope of the invention is not limited to the illustrated embodiments.

(First Embodiment: Ultrasonic Diagnostic Imaging System)

The ultrasonic diagnostic imaging system according to this embodiment is an ultrasonic diagnostic imaging system provided with an ultrasonic probe and an image processing section that converts a signal generated when the ultrasonic probe receives ultrasound reflected from an examinee to image information.

The system includes the following components.

More specifically, the system includes a measuring unit (may also be referred to as a "coordinate calculation section" in exemplary embodiments which will be described later) that measures a relative position and relative posture of the ultrasonic probe with respect to the examinee using image information on the examinee acquired by the ultrasonic probe.

Furthermore, the system also includes a control amount calculation unit that calculates an amount of control of the position and posture of the ultrasonic probe based on the measurement result of the measuring unit.

The system also includes at least one of a probe control mechanism that controls a position and posture of the ultrasonic probe using the amount of control calculated by the control amount calculation unit and a guiding information presentation unit that presents information for guiding movement of the position and posture of the ultrasonic probe using the amount of control calculated by the control amount calculation unit.

Here, the measuring unit can measure the relative position and relative posture based on the detection result of the region detection section that detects a specific region of the examinee. The region detection section can detect a region from the correspondence between information on the shape of the region of the examinee and the image information.

Furthermore, the system can include a database that records the relative position and relative posture between the ultrasonic probe and the examinee beforehand and the control amount calculation unit can calculate the amount of control using information on the database.

Here, the information on the relative position and relative posture between the ultrasonic probe and the examinee recorded in the database can be information that records a suitable probe state (position and posture or the like) for carrying out an ultrasonic image diagnosis.

The ultrasonic probe can have a pressure measuring unit that measures a pressure between the ultrasonic probe and the examinee. In such a case, the database can record information on the pressure between the ultrasonic probe and the examinee.

(Second Embodiment: Control Method)

The control method according to this embodiment is a control method for an ultrasonic diagnostic imaging system provided with an ultrasonic probe and an image processing section that converts a signal generated when the ultrasonic probe receives ultrasound reflected from the examinee to image information. More specifically, the method includes the following steps.

a) A measuring step of measuring a relative position and relative posture of the ultrasonic probe with respect to the examinee using image information on the examinee acquired by the ultrasonic probe b) A control amount calculation step of calculating an amount of control of the position and posture of the ultrasonic probe based on the measurement result of the measuring step Furthermore, the method includes at least one of e) and f) below.

e) A probe control step of controlling the position and posture of the ultrasonic probe using the amount of control calculated in the control amount calculation step f) A guiding information presentation step of presenting information for guiding movement of the position and posture of the ultrasonic probe using the amount of control calculated by the control amount calculation unit Furthermore, it is also an exemplary embodiment that the method includes a region detection step of detecting a specific region of the examinee, and in the measurement step, the relative position and relative posture are measured using the detection result in the region detection step.

In the region detection step, information on the shape of the examinee is included beforehand and the region can be detected through the correspondence with the image converted by the image processing section.

The method includes a database that records the relative position and relative posture between the ultrasonic probe and the examinee beforehand, and in the control amount calculation step, the amount of control can be calculated using the information on the database.

The information on the relative position and relative posture between the ultrasonic probe and the examinee recorded in the database can be information that records a state of the ultrasonic probe for carrying out an ultrasonic image diagnosis.

The ultrasonic probe may also be provided with a pressure sensor and a pressure measurement step of measuring a pressure between the ultrasonic probe and the examinee can further be added to the steps of the control method. In such a case, the database can record information on the pressure between the ultrasonic probe and the examinee.

Furthermore, the present invention includes a program to realize the aforementioned control method and a recording medium that records the program to realize the control method.

Hereinafter, the invention according to the above described embodiments will be described more specifically using exemplary embodiments.

Exemplary Embodiments (Exemplary Embodiment 1)

A: Overall Configuration

FIG. 1 illustrates an overview of an ultrasonic diagnostic imaging system, which is one of the embodiments of the present invention. The ultrasonic diagnostic imaging system of this exemplary embodiment includes an ultrasonic probe 1001, an ultrasonic diagnostic imaging apparatus 1002, a host controller 1003 and a probe position/posture control apparatus 1004. The ultrasonic probe 1001 is used so as to contact an examinee 1005 such as a human body. Furthermore, the ultrasonic probe 1001 is held by the probe position/posture control apparatus 1004. These apparatuses are mutually connected and operate by exchanging a control signal or the like through the connection. The probe position/posture control apparatus 1004 is necessary when automating the operation of the ultrasonic probe 1001 and is not indispensable to the aforementioned present invention. The exemplary embodiments which will be described later illustrate the configuration in the case where this probe position/posture control apparatus is not used. FIG. 1 describes the ultrasonic diagnostic imaging apparatus 1002 and the host controller 1003 as separate apparatuses, but it goes without saying that a configuration in which one is incorporated in the other may also be acceptable.

Figure 2:
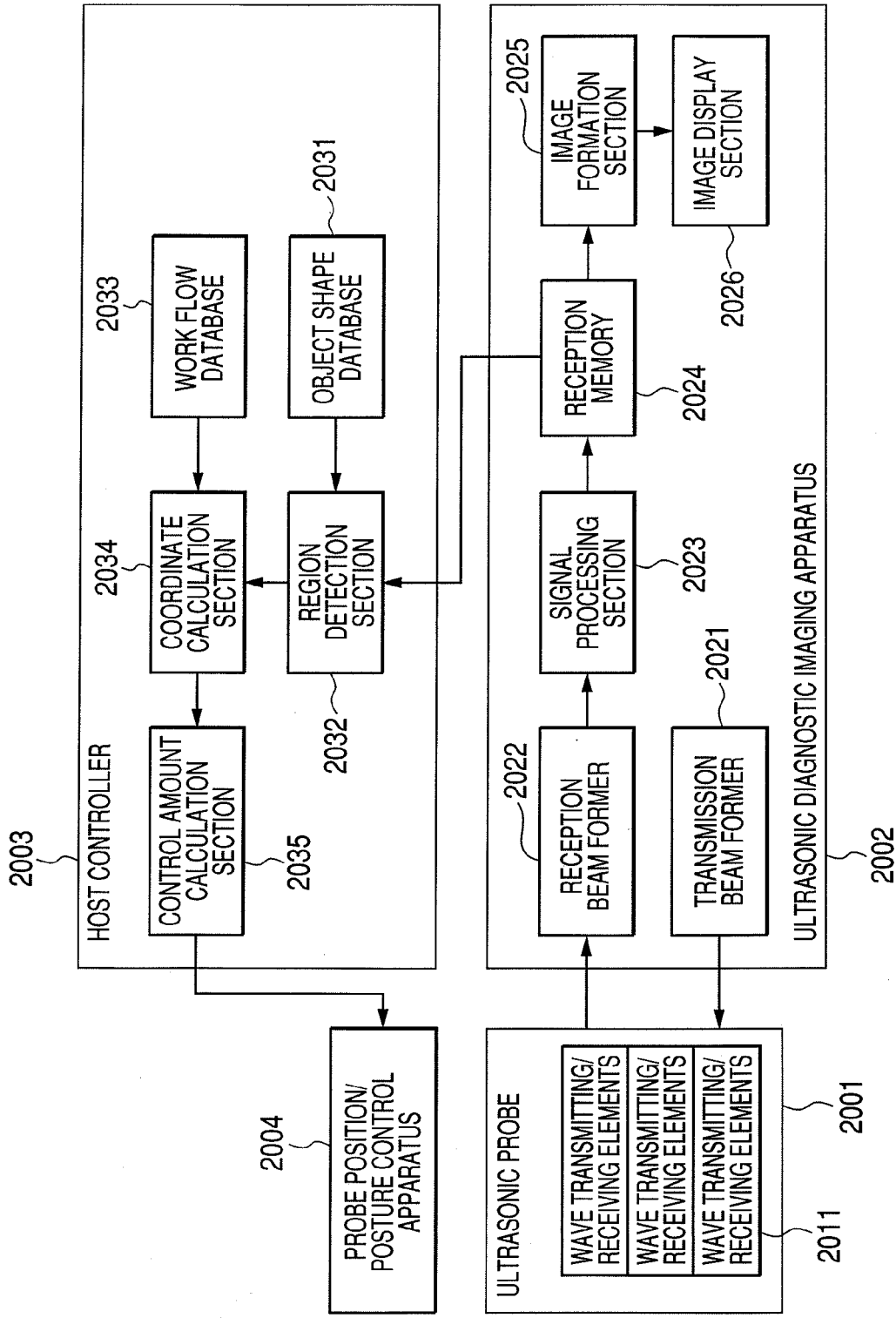
FIG. 2 is a configuration diagram of the ultrasonic diagnostic imaging system according to the present invention.

Next, the function and configuration of the ultrasonic diagnostic imaging system of this exemplary embodiment will be described using FIG. 2.

B: Ultrasound Probe

An ultrasonic probe 2001 is made up of a plurality of wave transmitting/receiving elements 2011 (ultrasonic resonators) that transmit ultrasonic pulses to the examinee 1005 and also receive signals reflected from the examinee.

The wave transmitting/receiving element 2011 can be made up of a piezoelectric element including a polymer piezoelectric element such as piezoelectric ceramic represented by PZT (lead zirconium titanate) and PVDF (polyvinyl difluoride). In this case, ultrasonic pulses can be generated by converting a time-varying electric signal to mechanical vibration through a piezoelectric element.

The ultrasonic probe 2001 can be configured by arranging the plurality of wave transmitting/receiving elements 2011 in a one-dimensional array. In this case, the ultrasonic probe 2001 can form a two-dimensional scanning plane in the space and can take cross-sectional images of the examinee. Furthermore, the ultrasonic probe 2001 can be configured by arranging the plurality of wave transmitting/receiving elements 2011 in a two-dimensional array. In this case, the ultrasonic probe 2001 can take images of three-dimensional voxel data of the examinee through three-dimensional and electronic scanning in the space.

C: Ultrasonic Diagnostic Imaging Apparatus

An ultrasonic diagnostic imaging apparatus 2002 is made up of a transmission beam former 2021, a reception beam former 2022, a signal processing section 2023, a reception memory 2024, an image formation section 2025 and an image display section 2026.

The transmission beam former 2021 forms ultrasound to be transmitted through the ultrasonic probe 2001 by controlling a transmission drive signal supplied to the plurality of wave transmitting/receiving elements 2011 of the ultrasonic probe 2001.

The reception beam former 2022 collects received wave data output by the wave transmitting/receiving element 2011 and forms echo data.

The signal processing section 2023 generates brightness data, blood flow velocity data and displacement data or the like based on the echo data formed by the reception beam former 2022.

The brightness data, blood flow velocity data and displacement data or the like formed by the signal processing section 2023 are written into the reception memory 2024. The written data is output to a host controller 2003. Furthermore, the data written into the reception memory data 2024 is also output to the image formation section 2025 in the ultrasonic diagnostic imaging apparatus 2002, the image formation section 2025 forms an ultrasound image and the image display section 2026 displays the ultrasound image.

D: Host Controller

The host controller 2003 is made up of an object shape database 2031, a region detection section 2032, a work flow database 2033, a coordinate calculation section (measuring unit) 2034 and a control amount calculation section 2035. However, all or some of the components of the host controller 2003 may also be incorporated in the ultrasonic diagnostic imaging apparatus 2002.

The object shape database 2031 is a unit that records information such as shape information on the inspection object. For example, data of a standard human body internal structure called a "human body atlas" can be used as the information to be stored in the object shape database.

The region detection section 2032 references the information stored in the object shape database 2031 and detects a region to be inspected from among ultrasound images input from the ultrasonic diagnostic imaging apparatus 2002. Various detection methods are available. Examples of the detection method include template matching and contour shape matching. More specific processing contents will be described in the procedure which will be described later.

The work flow database 2033 is a unit that stores information on the ultrasonic probe operation in an ultrasonic image diagnosis. The information to be stored in the work flow database can be, for example, data having information on a relationship of the relative position and posture between an appropriate region and the ultrasonic probe when the region is imaged using ultrasound for each region to be inspected.

The coordinate calculation section 2034 calculates the relationship of the relative position and posture between the region to be inspected and the ultrasonic probe 2001 based on the detection result of the region detection section 2032. This calculation can be performed as follows. For example, the relationship between the spatial coordinates relative to the ultrasonic probe 2001 and the image coordinates of the ultrasound image taken by the ultrasonic probe is determined beforehand. Determining the relationship beforehand in this way allows the relationship of the relative position and posture between the region to be inspected and the ultrasonic probe 2001 to be determined from the image coordinates in the ultrasound image of the region to be inspected detected by the region detection section 2032.

The control amount calculation section 2035 calculates the amount of control on the position and posture of the ultrasonic probe 2001. More specifically, the control amount calculation section 2035 uses information on the ultrasonic probe operation stored in the work flow database 2033 and the relationship of the relative position and posture between the ultrasonic probe 2001 and the region to be inspected calculated by the coordinate calculation section 2034.

E: Probe Position/Posture Control Apparatus

Figure 3:
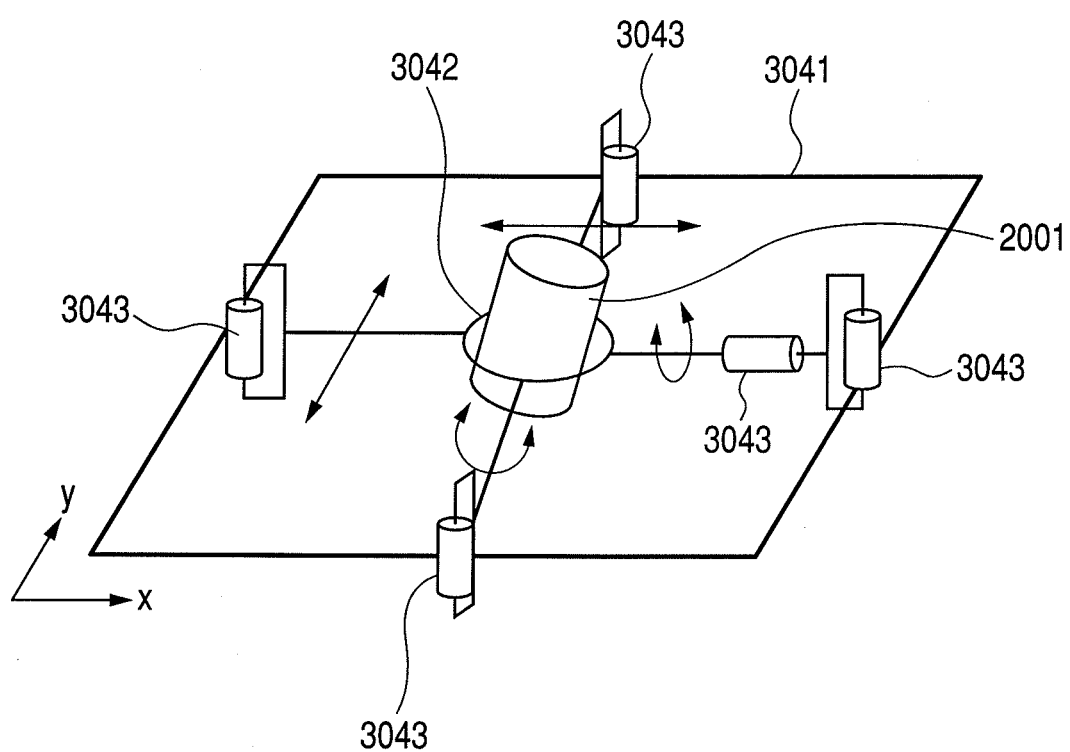
FIG. 3 is an outside view of the probe position/posture control apparatus in the present invention.

A probe position/posture control apparatus 2004 holds the ultrasonic probe 2001 using a mechanism that can move/rotate the ultrasonic probe 2001 and performs operation to move/rotate the ultrasonic probe 2001 according to the input from the host controller 2003. The probe position/posture control apparatus 2004 can be configured using a base frame 3041, a probe holder 3042 and a plurality of actuators 3043 as shown in FIG. 3 to realize this operation. In this case, the plurality of actuators 3043 are driven according to the input from the host controller 2003. As a result of changing the relationship of the relative position and posture between the base frame 3041 and probe holder 3042, the position and posture of the ultrasonic probe 2001 held by the probe holder 3042 is controlled. Of course, the probe position/posture control apparatus 2004 includes not only an apparatus that controls both the position and posture of the probe but also an apparatus that controls any one of the position and posture.

FIG. 3 illustrates the mechanism capable of carrying out operation with a total of four degrees of freedom; movement in each axial direction and rotation around each axis on the x-y plane of the base frame 3041 as an example, but in addition to this, a mechanism that also allows movement and rotation with respect to the z axis in the direction perpendicular to x-y can be adopted. This case results in the mechanism capable of carrying out operation with a total of 6 degrees of freedom. Furthermore, a mechanism having any number of degrees of freedom other than 4 and 6 degrees of freedom shown as examples can also be an embodiment of the present invention.

F: Description of Processing Flow

Figure 4:
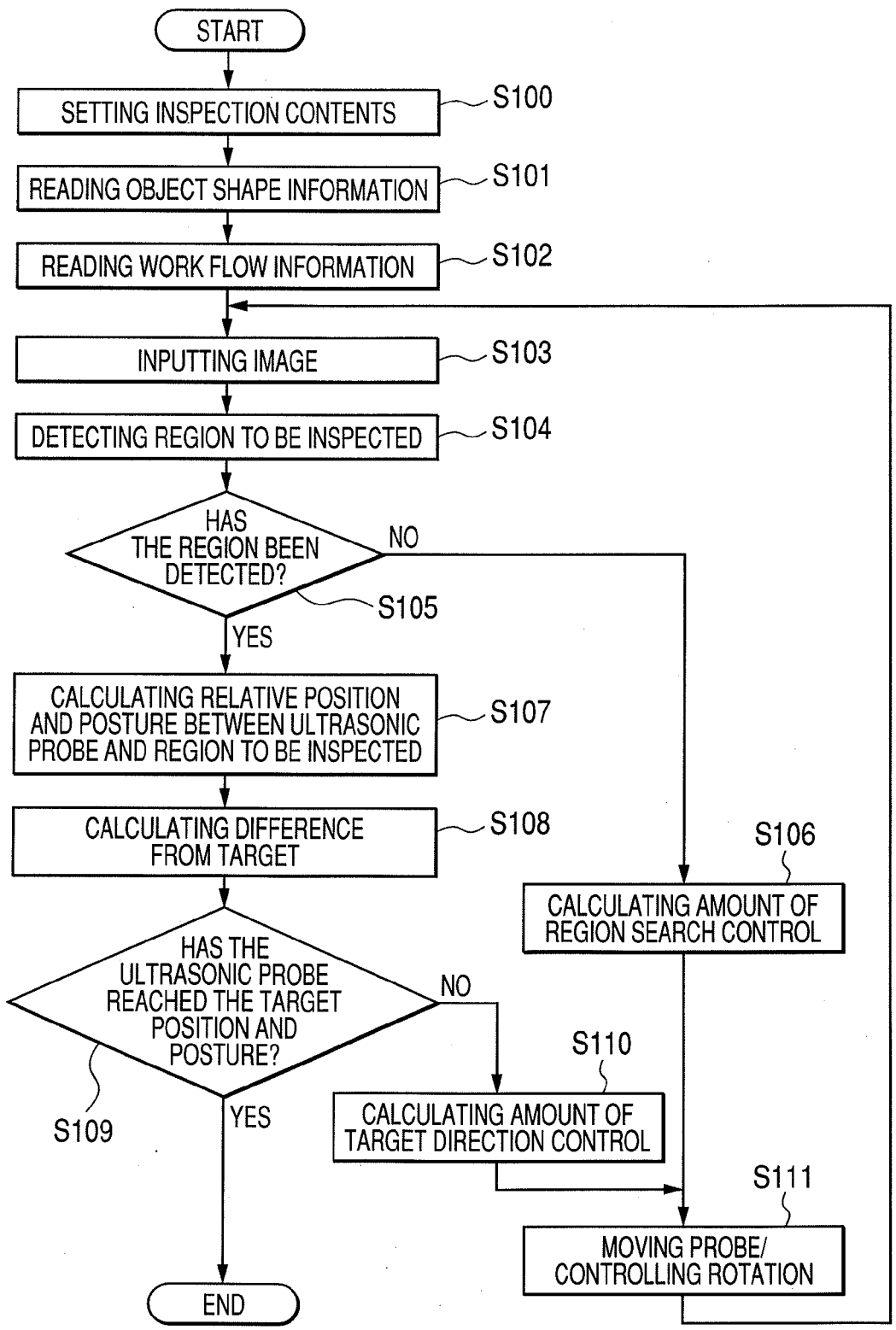
FIG. 4 is a flowchart illustrating a procedure of the ultrasonic diagnostic imaging system according to the present invention.

Next, a more specific procedure executed by the ultrasonic diagnostic imaging apparatus 2002 according to this embodiment will be described with reference to FIG. 4 and FIG. 2.

f1: Setting of Inspection Contents (Step S100)

First, the user sets inspection contents as step S100. For example, a plurality of buttons are arranged on an operation panel (not shown) provided on the host controller 2003 and inspection items are assigned to the buttons. Pressing each button allows the corresponding inspection contents to be set. In addition to this, for example, a list of inspection items may be shown on the image display section 2026 of the ultrasonic diagnostic imaging apparatus 2002 so as to allow the user to select an inspection item by operating the operation panel (not shown).

f2: Reading Object Shape Information (Shape DB) (Step S101)

Next, the information on the shape of the region to be inspected corresponding to the inspection item set in step S100 is read from the object shape database 2031 into the region detection section 2032. In this case, by recording various types of shape information which vary depending on the attributes such as age, sex, height and weight in the object shape database 2031 and also setting those attributes on the examinee to be inspected, it is possible to read shape information more suited to the examinee.

Figure 5:
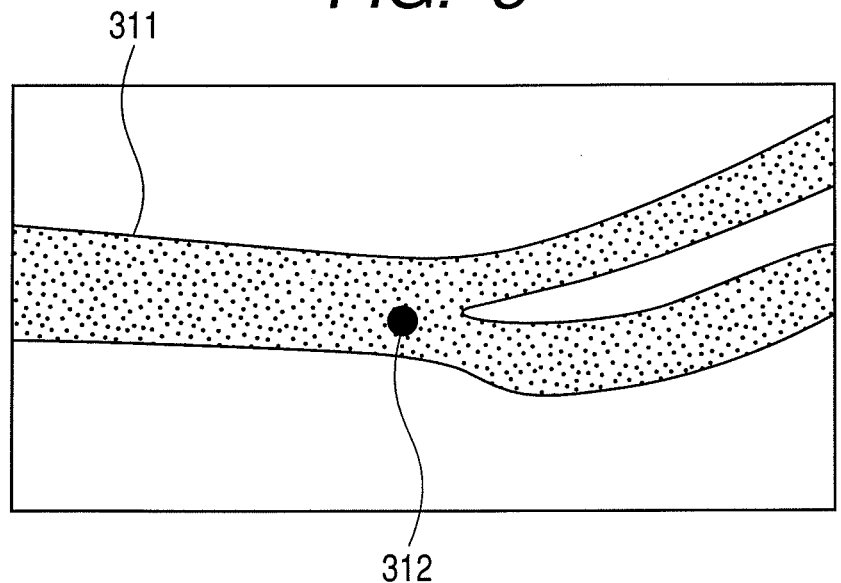
FIG. 5 illustrates information stored in the object shape database in the present invention.

This exemplary embodiment will describe a case where "inspection on arterial sclerosis of carotid artery" is set as an inspection item as an example. FIG. 5 shows an example of the information on the shape of the region to be inspected, which is read in this case. In this figure, a region to be inspected 311 shows the shape of the region to be inspected corresponding to the inspection contents set in step S100. Here, the case where the region to be inspected 311 has two-dimensional image information is described as an example, but the present invention is not limited to this and, for example, three-dimensional voxel data or the like may also be used. Furthermore, a reference point 312 is reference information on the position and posture added to the region to be inspected and referenced in the next and subsequent steps. When reading the above described information recorded in the object shape database 2031, the region detection section 2032 can read the information on the object shape database 2031 in the same format or also read the information after extracting the contour plane and contour lines of the region. Furthermore, information on the contour plane or contour lines of the region to be inspected can also be stored in the shape information database from the beginning.

f3: Reading Work Flow Database (Step S102)

Figure 6:
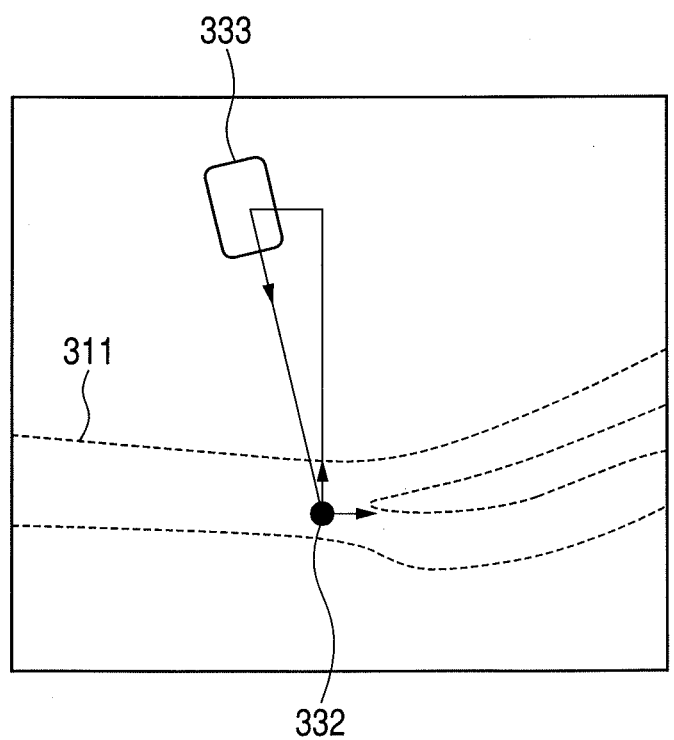
FIG. 6 illustrates information stored in the work flow database in the present invention.

Next, target values of the probe position and posture corresponding to the inspection items set in step S100 are read from the work flow database 2033. FIG. 6 shows an example of target values, which are read in this case. Here, a case where the work flow database stores the range of the relative position of the region to be inspected relative to the reference point and the range of the relative angle as target values of the probe position and posture is shown as an example.

In this figure, a region to be inspected 331 indicates the region to be inspected set in step S100. A reference point 332 indicates the position which becomes a base point of the target values of the probe position and posture. Furthermore, as indicated by the arrow in the figure, the reference point 332 also has information on the direction to be a reference. A probe target position/target posture 333 indicates the position state and posture state that should be taken by the ultrasonic probe 2001 when an ultrasound image is taken. All these states are read as numerical information using the reference point 332 as a reference.

f4: Image Input (Step S103)

Next, an ultrasound image is taken and the image is input. To take an ultrasound image, the transmission beam former 2021 of the ultrasonic diagnostic imaging apparatus 2002 forms and sends an electric signal to drive the wave transmitting/receiving element 2011 of the ultrasonic probe 2001.

The wave transmitting/receiving element 11 of the ultrasonic probe 2001 receives the ultrasound reflected and returned from within the examinee and the signal is input to the reception beam former 2022 of the ultrasonic diagnostic imaging apparatus 2002. The reception beam former 2022 performs processing such as superimposition on the received signal and inputs the signal to the reception memory 2024. The data input to the reception memory 2024 is displayed on the image display section 2026 through the image formation section 2025 and also input to the region detection section 2032 of the host controller 2003.

f5: Region Detection (Step S104)

Next, the region detection section 2032 detects the region to be inspected read from the object shape database 2031 from among the ultrasound images input from the ultrasonic diagnostic imaging apparatus 2002.

There are various methods of detecting the region to be inspected. Here, a method of applying contour extraction of an object to be imaged to the information on the ultrasound image and region shape database 2031 and detecting the region to be inspected based on matching between the contours will be described using FIGS. 7A, 7B, 7C, 7D and 7E.

Figure 7A:
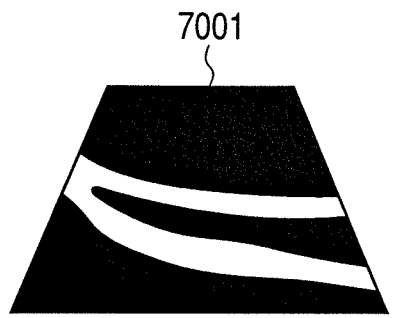
FIGS. 7A, 7B, 7C, 7D and 7E illustrate processing by the region detection section in the present invention.
Figure 7B:
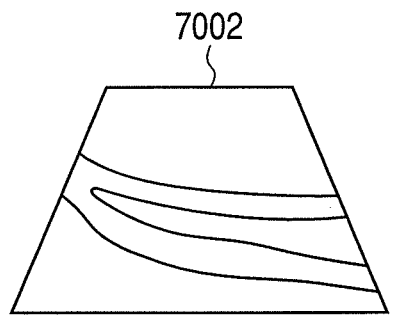
Figure 7C:
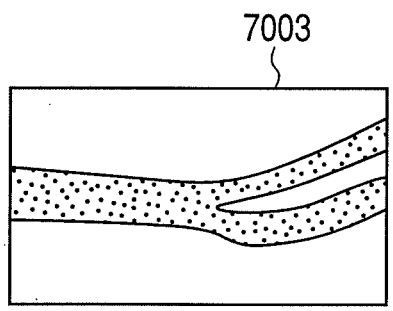
Figure 7D:
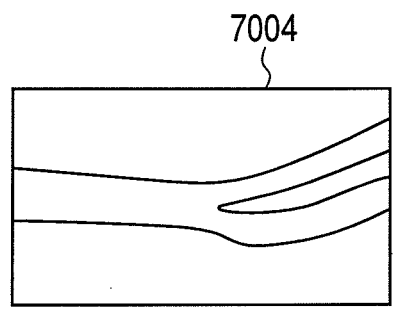

In FIGS. 7A to 7E, FIG. 7A shows an input ultrasound image 7001. Contour information 7002 as shown in FIG. 7B is obtained by applying contour extraction processing to this image. Furthermore, an image 7003 in FIG. 7C is information on the object shape database 2031 and contour information 7004 as shown in FIG. 7D is obtained by applying contour extraction to the image 7003.

Here, the contour information 7004 in FIG. 7D is superimposed on the contour information 7002 in FIG. 7B and the amount of movement/amount of rotation of FIG. 7D that corresponds to the maximum superimposition between the two pieces of information is searched (of course, the amount of movement/amount of rotation of the image FIG. 7B may also be searched).

Figure 7E:
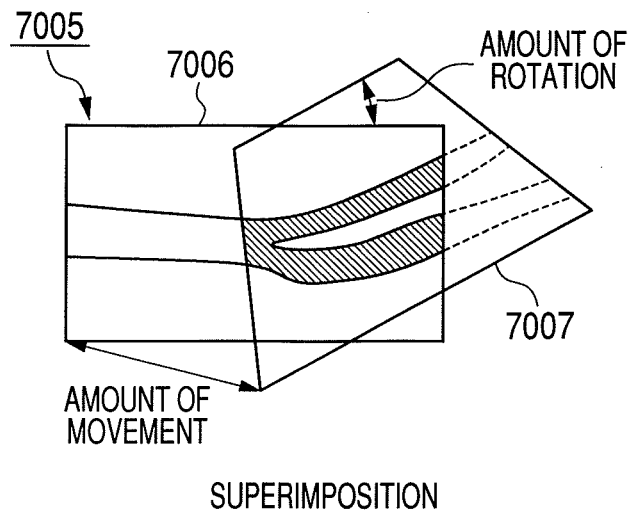

As a result, the amount of movement/amount of rotation corresponding to the maximum superimposition can be calculated as shown in 7005 in FIG. 7E. Here, the image 7006 corresponds to the image 7004 in FIG. 7D and the image 7007 corresponds to the image 7002 in FIG. 7B. Here, the procedure for detecting a region by applying contour extraction processing to both pieces of information on the ultrasound image and the region shape database and comparing the two contour shapes has been described.

However, the procedure for region detection in step S104 is not limited to this method.

For example, there can also be a procedure that detects a plurality of characteristic corners instead of carrying out contour extraction processing and detects the region through matching among those characteristic corners. Furthermore, there can also be a procedure for detecting the region by directly comparing pixel values between the ultrasound image and the object shape database 2031. In this case, the similarity among pixel values can be evaluated by indices such as correlation coefficients and mutual information content. Furthermore, more robust region detection can also be performed in consideration of deformation of the shape of the region.

With the above described procedure, the region similar to the shape information stored in the object shape database 2031 can be detected from the ultrasound image. Furthermore, the detection intensity using the similarity of both shapes as a reference and a relationship between positions where both shapes closely resemble each other can also be obtained simultaneously.

Here, the case where both the ultrasound image and the shape information stored in the object shape database 2031 are two-dimensional image data has been described, but the present invention is not limited to this. For example, at least one of the ultrasound image and the shape information stored in the object shape database 2031 may be three-dimensional voxel data. In such a case, the target region can be detected through matching between three-dimensional voxel data or matching between two-dimensional image data and three-dimensional voxel data.

f6: Determining Detection Result (Step S105)

In step S105, it is determined whether or not the region has been detected based on the result of the region detection carried out in step S104.

This determination can be made assuming, for example, that when the maximum value of the detection intensity obtained as a result of the region detection is greater than a preset threshold, the region to be inspected has been detected, whereas when smaller than the threshold, the region to be inspected has not been detected. In addition to this, when the detection intensity exceeds the threshold for several frames consecutively, it is also possible to determine that the region has been detected. In this case, there is an advantage that a determination can be made with higher reliability. Furthermore, a value that differs from one region to be inspected to another can also be set as the threshold. In this case, an appropriate threshold can be set in consideration of the difference between regions with and without large individual differences in shape.

When it is determined in step S105 that the region to be inspected has been detected, the process moves to step S107 or moves to step S106 otherwise.

f7: Calculating Amount of Region Search Control (Step S106)

In step S105, when the region to be inspected has not been detected from among the ultrasound images, control over the movement/rotation is performed so as to change the position and posture of the ultrasonic probe 2001 so that the inspection object falls within the imaging range. In this case, the simplest method for moving/rotating the ultrasonic probe 2001 may be the method of thoroughly scanning the movable range of the probe position/posture control apparatus 2004. For example, the ultrasonic probe 2001 is moved to the position of the farthest end of the probe position/posture control apparatus 2004 and a control signal is sent to the probe position/posture control apparatus so as to gradually move the ultrasonic probe 2001 while taking ultrasound images. If the region to be inspected is detected in the process, scanning of the position and posture of the ultrasonic probe is finished according to the determination result in step S105 and the process moves to step S107.

Furthermore, as another method, not only the region to be inspected but also the shapes of regions existing around and their relative positional relationship with the region to be inspected can be stored in the region shape database. Such storage allows the ultrasonic probe 1 to be moved or rotated according to the detection results of the peripheral regions even when the region to be inspected cannot be directly detected.

The more specific operation of the probe position/posture control apparatus 2004 will be described in detail in the description of step S111.

f8: Coordinate Calculation (Step S107)

Next, the coordinate calculation section 2034 (FIG. 2) calculates the relative position and posture between the ultrasonic probe 2001 and a reference point in the object shape database 2031.

This calculation is performed based on the following first and second relationships. The first relationship is a relationship between the spatial coordinates using the ultrasonic probe 2001 as a reference and the image coordinates of the ultrasound image taken. The second relationship is a correlation between the position and posture information on the image of the region to be inspected detected in step S104 and the reference coordinates stored in the object shape database 2031.

This processing will be described in detail using FIG. 8 and FIGS. 9A, 9B and 9C.

For simplicity of description here, suppose that all the real space, ultrasound image and shape information of the object shape database 2031 occupy a two-dimensional space. However, the present invention is not limited to this and when, for example, all or part of the information occupies a three-dimensional space, the present invention can be implemented by a simple extension in the following description.

Figure 8:
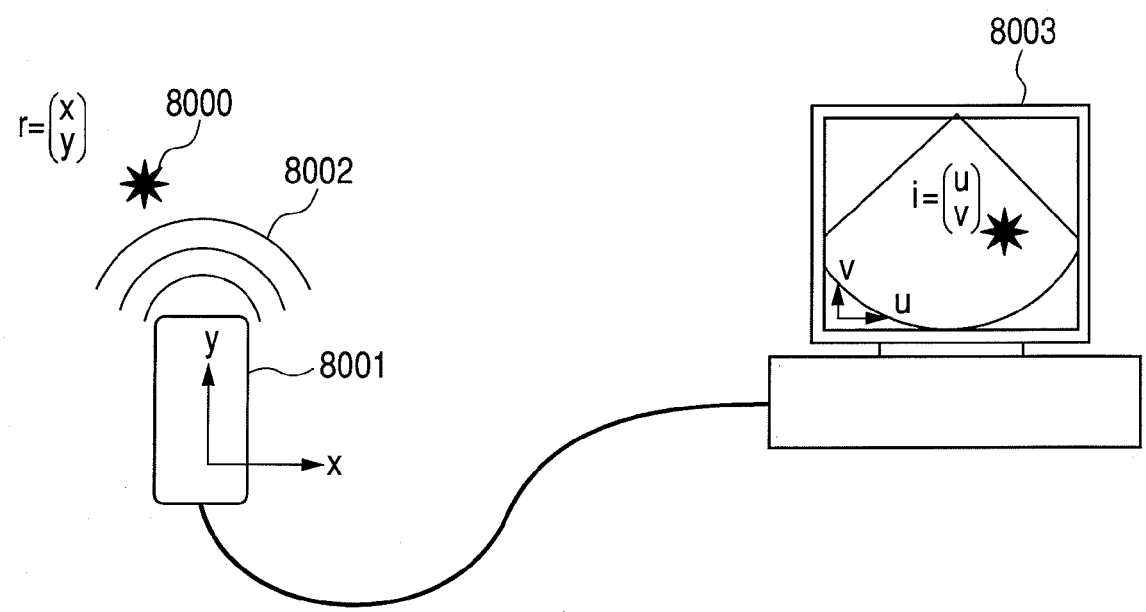
FIG. 8 illustrates a relationship between the ultrasonic probe and an ultrasound image in the present invention.
Figure 9A:
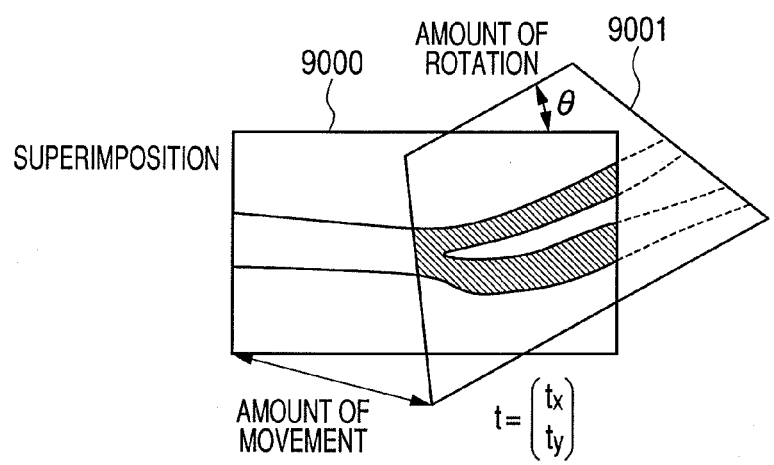
FIGS. 9A, 9B and 9C illustrate relationships between an ultrasound image and information on the object shape database in the present invention.
Figure 9B:
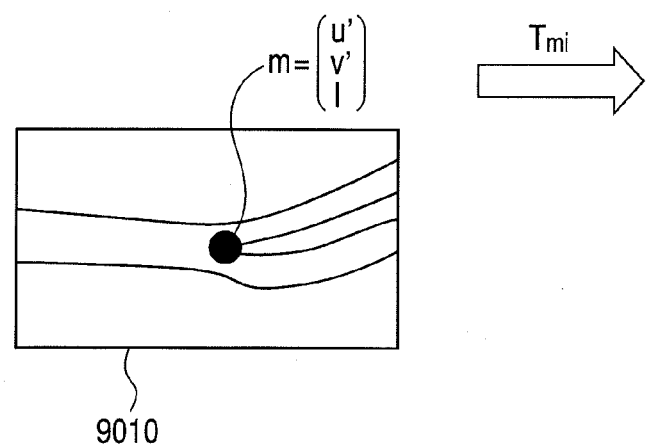
Figure 9C:
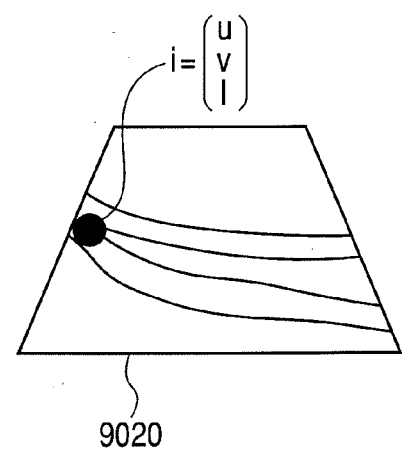

FIG. 8 illustrates a relationship between coordinates of the real space in which an imaging object exists and those of an ultrasound image generated through ultrasonic imaging. Reference numeral 8001 schematically denotes an ultrasonic probe, 8002 denotes ultrasound, 8003 denotes a host controller and 8000 denotes a measurement target.

In this figure, coordinates on an image are expressed by vector $i=(u\ v)^t$, coordinates in the real space are expressed by vector $r=(x\ y)^t$. Here, "t" added at the shoulder of the vector represents transposition. Suppose the coordinate vector i represents a pixel point on an image located at the uth position in the rightward direction and with position in the downward direction on the screen relative to the origin assuming the left top end point of the image as the origin $(0\ 0)^t$. Furthermore, the coordinate vector r has the origin $(0\ 0)^t$ inside the ultrasonic probe 8001 and expresses a point in the real space which is moved by x[mm] and y[mm] respectively relative to the origin with respect to two mutually orthogonal axes that form an imaging plane.

The ultrasonic diagnostic imaging apparatus 2002 (FIG. 2) generates ultrasound from the ultrasonic probe 2001 (FIG. 1) and determines a brightness value at a point i on the ultrasound image based on the observed value of the reflected signal from a point r in the real space. Here, the correspondence between the point r in the real space and point i on the ultrasound image is expressed by the following expression using a function $T_{ri}$.

$$i = T_{ri}(r) \quad \text{(Expression 1)}$$

Here, assuming that the coordinate vector i has a linear relationship with respect to the coordinate vector r, i can be expressed as:

$$i = T_{ri} r \quad \text{(Expression 2)}$$

where $T_{ri}$ represents a matrix expressing the linear relationship between i and r, and i and r are redefined as extended vectors $i=(u\ v\ 1)^t$ and $r=(x\ y\ 1)^t$ respectively. Normally, the assumption of the above described linear relationship sufficiently holds in a calibrated ultrasonic diagnostic imaging apparatus. Furthermore, on the contrary, transformation from the point i on the image to the point r in the real space can be expressed using an inverse matrix $T_{ri}^{-1}$ the matrix $T_{ri}$ as:

$$r = T_{ri}^{-1} i \quad \text{(Expression 3)}$$

Since the matrix $T_{ri}$ is a regular matrix except special cases, the inverse matrix $T_{ri}^{-1}$ can be calculated.

On the other hand, the correspondence between the point i on the ultrasound image and the point of the object shape database 2031 is obtained from the processing result in step S104. This will be described using FIGS. 9A, 9B and 9C. 9000 and 9001 in FIG. 9A correspond to 7006 and 7007 in FIGS. 7A, 7B, 7C, 7D and 7E respectively. First, suppose the point in the object shape database 2031 with respect to the point i on the ultrasound image is vector $m=(u'\ v'\ 1)^t$. On the assumption that vector m (FIG. 9B 9010) and vector i (FIG. 9C 9020) have a linear relationship, i can be expressed using a linear transformation matrix $T_{mi}$ as:

$$i = T_{mi} m \quad \text{(Expression 4)}$$

Furthermore, the relationship with the point r in the real space corresponding to an arbitrary point m in the object shape database 2031 can be expressed using Expression 3 and Expression 4 as:

$$r = T_{ri}^{-1} T_{mi} m \quad \text{(Expression 5)}$$

Here, assuming that the point m represents coordinates of a region reference point of the object shape database 2031, the corresponding point in the real space can be determined as a coordinate r using the ultrasonic probe 2001 as a reference.

Here, the example has been described where the position of the region reference point of the object shape database 2031 is determined in a coordinate system using the ultrasonic probe 2001 as a reference, but to the contrary, the position and posture of the ultrasonic probe may also be determined using the region reference point of the object shape database 2031 as a reference.

f9: Calculating Difference from Target (Step S108)

As the next step, the coordinate calculation section 2034 further calculates a correspondence between the position and posture of the ultrasonic probe 2001 and the target position and posture read from the work flow database 2033. To calculate this correspondence, a correspondence between the position and posture of the reference point of the region to be inspected in the coordinate system using the ultrasonic probe 2001 obtained in step S107 as a reference and the target position and posture of the work flow database 2033 is determined. This processing will be described in detail using FIG. 10.

Figure 10:
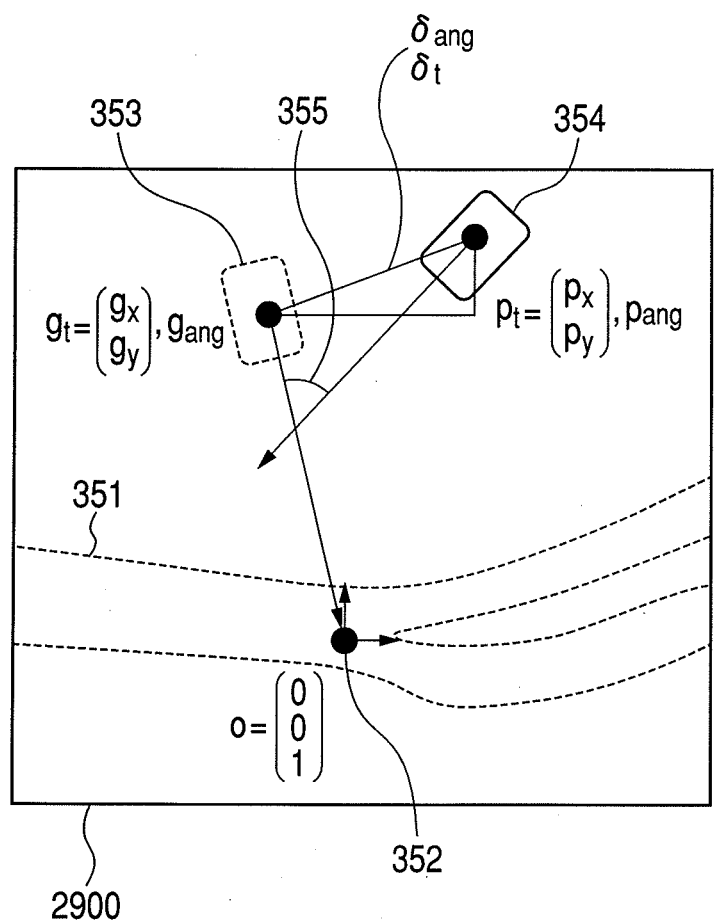
FIG. 10 illustrates processing by the coordinate calculation section in the present invention.

FIG. 10 illustrates the target position and posture of the ultrasonic probe stored in the work flow database and the current position and posture of the ultrasonic probe. Here, a region to be inspected 351, a reference point 352, a probe target position and posture 353 are the information read in step S102.

Furthermore, the region to be inspected 351 and reference point 352 can be assumed to express the same contents as the region to be inspected 311 and reference point 312 out of the information stored in the region shape database 2031 read in step S101.

In FIG. 10, the probe target position and posture 353 means the target values of the position and posture of the probe in the coordinate system whose origin is the reference point 352 of the region to be inspected. Here, the probe target position and posture 353 are divided into components of translational motion and rotation, and expressed as $g_t$ and $g_{ang}$ respectively. Similarly, the probe current position and posture 354 can also be expressed as $p_t$ and $p_{ang}$ respectively based on the relative position and posture with respect to the reference point of the ultrasonic probe and region to be inspected already determined in 5107. From the information, the difference in position $\delta_t$ between the current ultrasonic probe and the target, and difference in posture $\delta_{ang}$ can be calculated from the following expressions respectively.

$$\delta_t = p_t - g_t \quad \text{(Expression 6)}$$

$$\delta_{ang} = p_{ang} - g_{ang} \quad \text{(Expression 7)}$$

Through the above described processing, the degree of deviation in position/angle of the ultrasonic probe 2001 from the target position and posture at the present moment can be calculated.

f11: Determining Reach of Target (Step S109)

Next, it is determined whether or not the ultrasonic probe has reached the target position and posture based on the relative difference of the current position and posture of the ultrasonic probe from the target value calculated in step S108. As the method for determining this, the ultrasonic probe may be determined as having reached the target when the difference between the current position/posture of the ultrasonic probe 1 calculated in step 5108 and the target value is smaller than a predetermined threshold and determined as not having reached the target otherwise.

Furthermore, a value that varies depending on the setting of the region to be inspected may also be automatically set for this threshold. In this case, the target range of the position/posture of the ultrasonic probe can be changed for each inspection object.

f12: Calculating Amount of Target Direction Control (Step S110)

When the determination result in step S109 shows that the probe position/posture falls short of the target value, step S110 is carried out. In step S110, the control amount calculation section 2035 calculates the amount of control to be sent to the probe position/posture control apparatus so as to make the probe position/posture closer to the target value. Calculation of the amount of control can take various modes depending on the characteristic of the control apparatus. When, for example, the direction of movement/rotation is specified for the probe position/posture control apparatus and constant-speed drive is performed, the direction can be determined based on the positive/negative sign of each component value of the position difference $\delta_t$ and the posture difference $\delta_{ang}$ from the target value calculated in step S108.

As another method, the amount of control can also be calculated using both the signs and absolute values of the differences $\delta_t$ and $\delta_{ang}$ from the target value. In this case, there can be a method of determining the direction of control based on, for example, the signs of the difference values and determining the speed based on the absolute values.

f13: Probe Movement/Rotation Control (Step S111)

In step S111, the amount of control calculated in step S106 or step S110 is input to the ultrasonic probe position/posture control apparatus 2004 (FIG. 2) and the position and posture of the ultrasonic probe are driven so as to approximate to the target values. For example, based on the amount of control over the position and posture of the probe calculated in step S110, a voltage proportional, for example, to the amount of control is applied to the corresponding actuators 3043 (FIG. 3). In this way, the actuators 3043 are driven in the direction approximating to the target position and posture recorded in the work flow database 2033, and as a result, the ultrasonic probe 2001 held approximates to the target state.

Performing the processing from step S100 to step S111 described above can keep the ultrasonic probe 2001 in an appropriate position and posture with respect to the region to be inspected. By so doing, it is possible to provide an ultrasonic diagnostic imaging apparatus that allows even a user who has not special skill about ultrasonic imaging to take an ultrasound image suitable for a diagnosis.

This exemplary embodiment has described the case where the probe position/posture control apparatus 2004 mechanically moves/rotates the position and posture of the ultrasonic probe 2001 to realize ultrasonic imaging of a region to be inspected from the appropriate position/angle as an example. However, the embodiment of the present invention is not limited to this. When, for example, an ultrasonic probe having a plurality of wave transmitters/receivers capable of electronically changing the position/direction of transmission/reception of an ultrasound signal is used, making the wave transmission/reception position and direction of the ultrasound signal the control targets can produce the effects similar to those of the above described embodiment. Moreover, a configuration combining both mechanical control and electronic control also becomes one embodiment of the present invention.

(Exemplary Embodiment 2)

Exemplary Embodiment 1 has described the example where the ultrasonic probe is moved/rotated so as to guide the ultrasonic probe to an appropriate position and posture with respect to an object of ultrasound inspection, but the embodiment of the present invention is not limited to this.

For example, there can also be an embodiment of presenting navigation to urge the user to move/rotate the ultrasonic probe instead of providing an apparatus for moving/rotating the ultrasonic probe. An example of adopting such an embodiment will be described.

A: Overall Configuration

Figure 11:
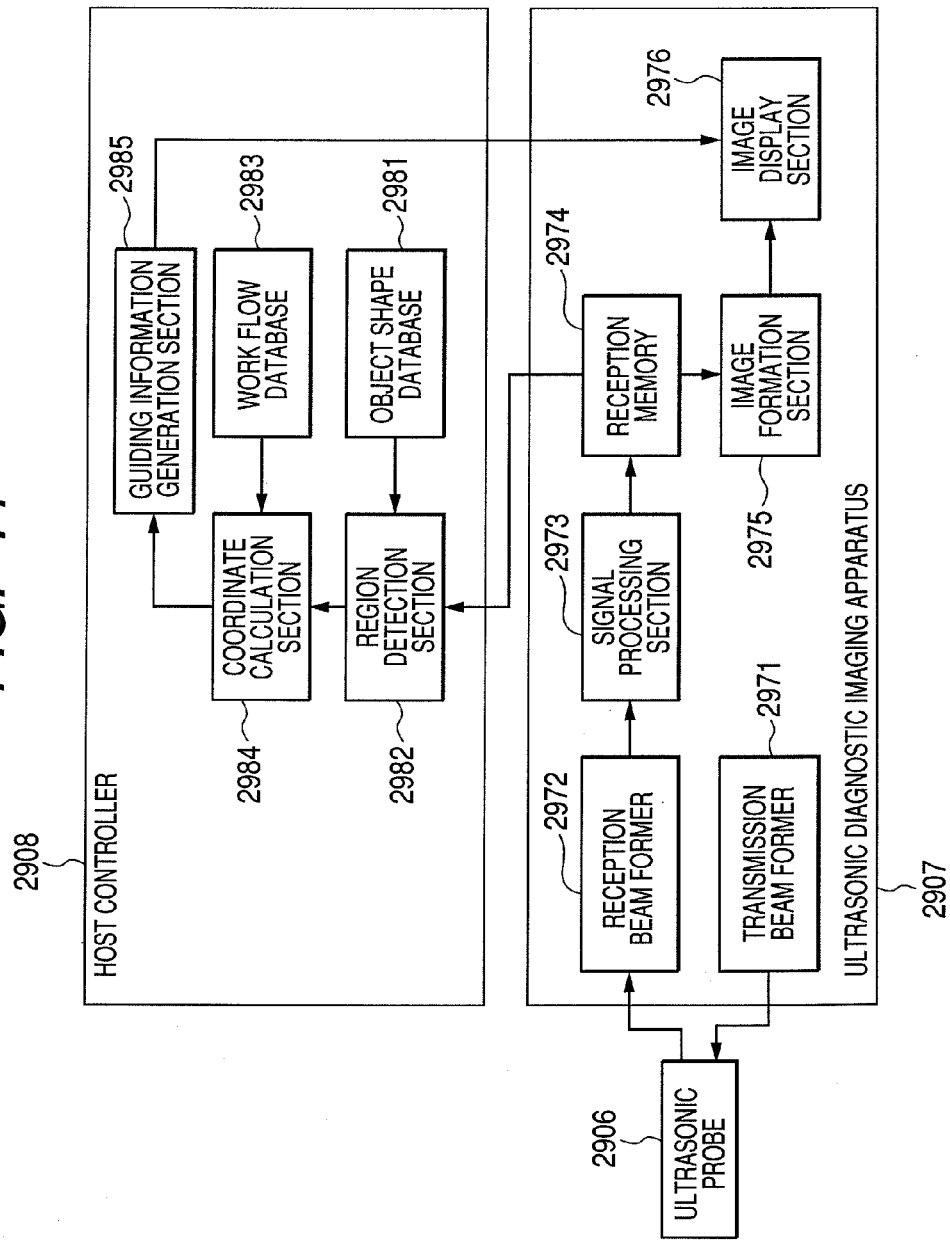
FIG. 11 is a configuration diagram of another ultrasonic diagnostic imaging system according to the present invention.

FIG. 11 illustrates the configuration of the exemplary embodiment presenting navigation to move/rotate the ultrasonic probe to the user.

The ultrasonic diagnostic imaging system of this embodiment is made up of an ultrasonic probe 2906, an ultrasonic diagnostic imaging apparatus 2907 and a host controller 2908.

B: Ultrasound Probe

Since the ultrasonic probe 2906 is similar to that in Exemplary Embodiment 1, descriptions thereof will be omitted.

C: Ultrasonic Diagnostic Imaging Apparatus

The ultrasonic diagnostic imaging apparatus 2907 is made up of a transmission beam former 2971, a reception beam former 2972, a signal processing section 2973, a reception memory 2974, an image formation section 2975 and an image display section 2976.

The image display section 2976 presents ultrasound image and navigation information based on signals from the image formation section 2975 and host controller 2908. Since the rest of the configuration included in the ultrasonic diagnostic imaging apparatus 2907 is similar to that described in Exemplary Embodiment 1, descriptions thereof will be omitted.

D: Host Controller

The host controller 2908 is made up of an object shape database 2981, a region detection section 2982, a work flow database 2983, a coordinate calculation section 2984 and a guiding information generation section 2985.

However, all or some of the components of the host controller 2908 can also be incorporated in the ultrasonic diagnostic imaging apparatus 2907. The guiding information generation section 2985 generates guiding information on the movement/rotation of the probe to be carried out by the user based on the difference from the target value of the probe calculated by the coordinate calculation section 2984. The guiding information generated is sent to the image display section 2976 of the ultrasonic diagnostic imaging apparatus 2907 and presented to the user using a display or the like. The rest of the configuration included in the host controller 2908 is the same as that described in Exemplary Embodiment 1, and therefore descriptions thereof will be omitted.

E: Guiding Information Generation Section

Figure 12A:
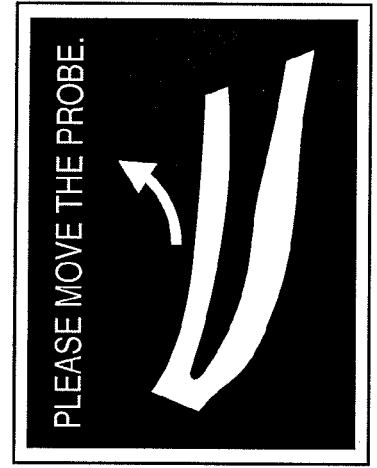
FIGS. 12A and 12B illustrate presentation examples of the guiding information in the present invention.
Figure 12B:
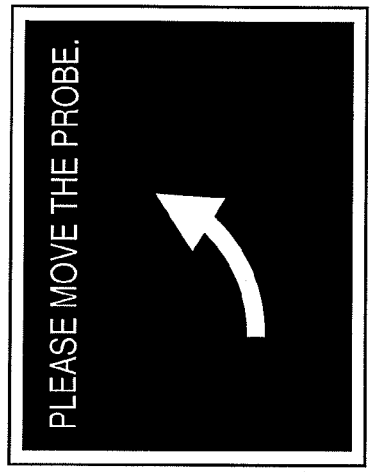

The guiding information generated by the guiding information generation section 2985 and presented by the image display section 2976 can be presented using symbols like an arrow as shown, for example, in FIG. 12A. Furthermore, as shown in FIG. 12B, the image display section 2976 may be enabled to present an ultrasound image and present guiding information simultaneously.

Furthermore, the presentation of the guiding information is not limited to the presentation by the image display section 2976 of the ultrasonic diagnostic imaging apparatus 2907. For example, the ultrasonic probe 2906 may be newly provided with a display section for presenting guiding information on the position and posture to enable guiding information to be presented. In this case, the user has the merit of being able to intuitively recognize the probe moving direction without referencing the ultrasonic diagnostic imaging apparatus 2907.

Furthermore, the guiding information of this exemplary embodiment is not limited to presentation with an image. As another configuration example, the host controller 2908 or ultrasonic diagnostic imaging apparatus 2907 or ultrasonic probe 2906 may be newly provided with a sound presentation section such as a speaker and the navigation generation section 2985 may be enabled to create guiding information with speech. In this case, the user can obtain the guiding information without viewing the screen.

(Exemplary Embodiment 3)

Exemplary Embodiment 1 and Exemplary Embodiment 2 have described the case where the host controller includes the database that stores information on the region to be inspected and the ultrasound inspection work flow as an example. However, the present invention is not limited to this embodiment.

Exemplary Embodiment 3 will describe an example of an ultrasound diagnostic system that acquires information on the region to be inspected and the ultrasound inspection work flow with reference to an external database.

Figure 13:
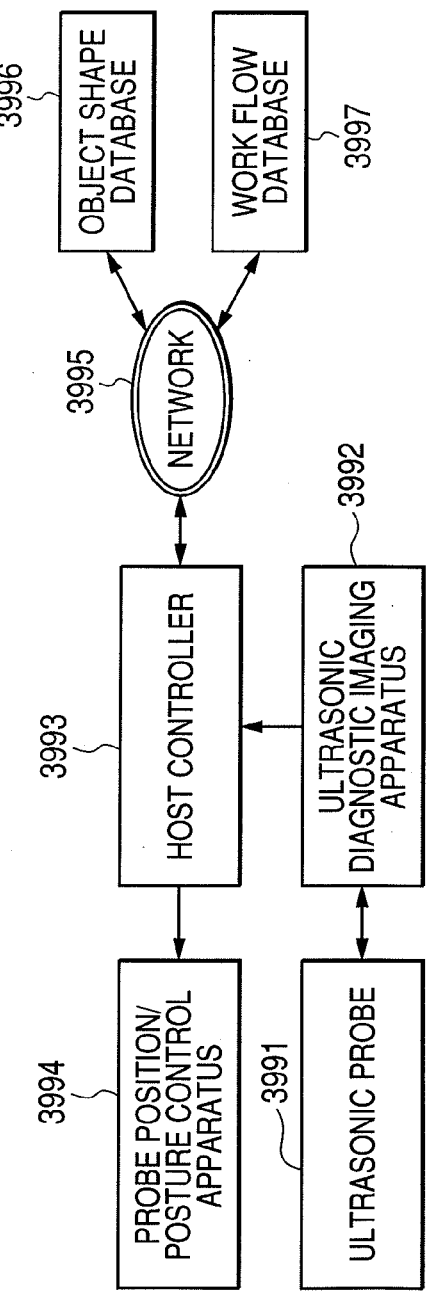
FIG. 13 is a configuration diagram of a further ultrasonic diagnostic imaging system according to the present invention.

FIG. 13 is a configuration diagram of an ultrasonic diagnostic imaging system according to this exemplary embodiment that acquires information from an external database via a network. The ultrasonic diagnostic imaging system according to this exemplary embodiment is made up of the following components. More specifically, the ultrasonic diagnostic imaging system is made up of an ultrasonic probe 3991, an ultrasonic diagnostic imaging apparatus 3992, a host controller 3993, a probe position/posture control apparatus 3994, an object shape database 3996 and a work flow database 3997.

Furthermore, the host controller 3993 is connected to the object shape database 3996 and the work flow database 3997 via a network 3995.

Here, a case where both the object shape database 3996 and work flow database 3997 are connected to the host controller 3993 via the network is described as an example, but the embodiment of the present invention is not limited to this.

For example, such a configuration may also be adopted that only one of the object shape database 3996 and the work flow database 3997 is connected via the network and the other is located inside the host controller 3993. Moreover, a connection via the network 3995 is shown as an example of connection, but the mode of connection may also be a so-called LAN connection or other connection modes such as USB connection, serial connection or parallel connection. Furthermore, the object shape database 3996 or work flow database 3997 and host controller 3993 need not always be paired. For example, depending on the embodiment, such a mode may also be adopted that the host controllers 3993 of a plurality of ultrasonic diagnostic imaging systems share the object shape database 3996 or the work flow database 3997.

Adopting the above described configuration eliminates the necessity for the ultrasound diagnostic system of the present invention to store necessary region shape information or work flow information in the host controller 3993 and enables a database supplied to the system to be flexibly expanded or changed.

Moreover, the host controller may also be configured so that the information stored in the object shape database 3996 and work flow database 3997 can be added, changed or deleted through an external operation. In this case, it is possible to flexibly update the database associated with expansion of the corresponding inspection items and revision of the inspection method or the like.

(Other Embodiments)

Furthermore, it goes without saying that the object of the present invention can also be attained by supplying a recording medium that records software program code to realize the functions of the aforementioned embodiments and exemplary embodiments to the system or apparatus. More specifically, a computer (or CPU or MPU) of the system or the apparatus reads and executes the program code stored in the recording medium. In this case, the program code itself read from the recording medium realizes the functions of the aforementioned embodiments and the recording medium storing the program code constitutes the present invention.

The functions of the aforementioned embodiments are realized by the computer executing the read program code, but the present invention does not include only such a case. It goes without saying that the present invention also includes a case where based on instructions of the program code, the operating system (OS) operating on the computer performs part or whole of actual processing and realizes the functions of the aforementioned embodiments.

Furthermore, it goes without saying that the present invention also includes a case where the functions of the aforementioned embodiments are realized through the processing performed in A) and B) below.

A) The program code read from the recording medium is written into a memory provided for a feature expansion card inserted in the computer or a feature expansion unit connected to the computer.

B) Based on instructions of the program code, a CPU provided for the feature expansion card or feature expansion unit then performs part or whole of the actual processing.

When the present invention is applied to the above described recording medium, the recording medium stores the program code corresponding to the flowchart described above.

The descriptions in the aforementioned embodiments are only examples of the preferred ultrasonic diagnostic imaging apparatus according to the present invention and the present invention is not limited to these examples.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2007-226340, filed Aug. 31, 2007, which is hereby incorporated by reference in its entirety.

The invention claimed is:

1. A diagnostic imaging system provided with a probe for detecting, from an examinee, an acoustic wave for generating an electric signal, and an image processing section for converting the generated signal into image information, the system comprising:
 a region detection unit configured to detect a specific region from an ultrasonic image of the examinee, wherein the specific region is not a target region to be medically inspected;
 a measuring unit configured to measure a relative position of the probe with respect to the examinee, based on a detection result from the region detection unit;
 a control amount calculation unit configured to calculate an amount of control of the position of the probe, based on a measurement by the measuring unit;
 a display control unit configured to control a display unit to display, in a case that the region detection unit detects the specific region, information for guiding the probe to the target region, based on the amount of control calculated by the control amount calculation unit; and
 a generation unit configured to generate, in a case that the specific region is not detected, a signal for moving the probe to search for the specific region.

2. The diagnostic imaging system according to claim 1, wherein the region detection unit obtains attribute information of the examinee, and searches a database for shape information corresponding to the attribute information, and detects the specific region based on correspondence between the shape information and the image information.

3. The diagnostic imaging system according to claim 1, wherein the specific region corresponds to a region to be inspected, and wherein the control amount calculation unit obtains, from a database, information on a relative positional relationship between the specific region and the region to be inspected, and calculates the position and posture of the probe to photograph the region to be inspected, based on the information on the relative positional relationship and the detection result from the region detection unit.

4. The diagnostic imaging system according to claim 1, further comprising a database configured to record information on relative positions and relative postures between the probe and the examinee beforehand,
 wherein the control amount calculation unit calculates the amount of control using the information recorded in the database.

5. The diagnostic imaging system according to claim 4, wherein the information recorded in the database indicates a state of the probe to make an ultrasonic image diagnosis.

6. The diagnostic imaging system according to claim 4, wherein the database records information on a pressure between the probe and the examinee.

7. The diagnostic imaging system according to claim 1, further comprising the probe, and
wherein the probe comprises a pressure measuring unit configured to measure a pressure between the probe and the examinee.

8. An diagnostic imaging system provided with a probe for detecting, from an examinee, an acoustic wave for generating an electric signal, and an image processing section for converting the generated signal into image information, the system comprising:
a region detection unit configured to detect a specific region from an ultrasonic image of the examinee, wherein the specific region is not a target region to be medically inspected;
a measuring unit configured to measure a relative position of the probe with respect to the examinee, based on a detection result from the region detection unit;
a control amount calculation unit configured to calculate an amount of control of the position of the probe, based on a measurement by the measuring unit; and
a probe control mechanism configured to control a position of the probe, using the amount of control calculated by the control amount calculation unit,
wherein, in a case that the specific region is not detected, the probe control mechanism controls the position of the probe to search for the target region, and
wherein the region detection unit detects the specific region, based on image information obtained in accordance with a control operation for a search for the specific region by the probe control mechanism.

9. The diagnostic imaging system according to claim 8, wherein the region detection unit obtains attribute information of the examinee, and searches a database for shape information corresponding to the attribute information, and detects the specific region based on a correspondence between the shape information and the image information.

10. The diagnostic imaging system according to claim 8, wherein the specific region corresponds to a region to be inspected, and
wherein the control amount calculation unit obtains, from a database, information on a relative positional relationship between the specific region and the region to be inspected, and calculates the position and a posture of the probe to photograph the region to be inspected, based on the information on the relative positional relationship and the detection result from the region detection unit.

11. The diagnostic imaging system according to claim 8, further comprising a database configured to record information on relative positions and relative postures between the probe and the examinee beforehand,
wherein the control amount calculation unit calculates the amount of control using the information recorded in the database.

12. The diagnostic imaging system according to claim 11, wherein the information recorded in the database indicates a state of the probe to make an ultrasonic image diagnosis.

13. The diagnostic imaging system according to claim 11, wherein the database records information on a pressure between the probe and the examinee.

14. The diagnostic imaging system according to claim 8, further comprising the probe, and
wherein the probe comprises a pressure measuring unit configured to measure a pressure between the probe and the examinee.

15. A method of controlling an diagnostic imaging system provided with a probe for detecting, from an examinee, an acoustic wave for generating an electric signal, and an image processing section for converting the generated signal into image information, the method comprising steps of:
detecting a specific region from an ultrasonic image of the examinee, wherein the specific region is not a target region to be medically inspected;
measuring a relative position of the probe with respect to the examinee, based on a detection in the detecting step;
calculating an amount of control of the position of the probe, based on a measurement obtained in the measuring step;
presenting, in a case that the specific region is detected, information for guiding the probe to the target region, based on the amount of control determined in the calculating step; and
generating, in a case that the specific region cannot be detected in the detecting step, a signal for moving the probe to search for the target region.

16. A non-transitory computer-readable storage medium storing a computer program that causes a computer to execute the method according to claim 15.

17. A method of controlling an diagnostic imaging system provided with a probe for detecting, from an examinee, an acoustic wave for generating an electric signal, and an image processing section for converting the generated signal into image information, the method comprising steps of:
detecting a specific region from an ultrasonic image of the examinee, wherein the specific region is not a target region to be medically inspected;
measuring a relative position of the probe with respect to the examinee, based on a detection in the detecting step;
calculating an amount of control of the position of the probe, based on a measurement obtained in the measuring step;
controlling a position of the probe, using the amount of control determined in the calculating step;
in a case that the specific region cannot be detected in the detecting step, controlling the position of the probe to search for the target region; and
detecting the specific region, based on image information obtained in accordance with a control operation for searching for the specific region.

18. A non-transitory computer-readable storage medium storing a computer program that causes a computer to execute the method according to claim 17.

19. An information processing apparatus for ultrasound imaging, comprising:
a first detection unit configured to detect a region to be medically inspected based on an image obtained from a probe;
a second detection unit configured to detect another region from an ultrasonic image, different from the region to be medically inspected;
a storage unit configured to store information indicating a relative positional relationship between the region to be medically inspected and the other region; and
an obtaining unit configured to obtain information for moving the probe to the region to be medically inspected, based on one of (a) a detection result provided by the first detection unit and (b) both a detection result provided by the second detection unit and the stored information.

20. The information processing apparatus according to claim 19, further comprising:
a region detection unit that detects a specific region of the examinee; and
a measuring unit configured to measure the relative position and a relative posture based on a detection result provided by the region detection unit.

21. The information processing apparatus according to claim 20, wherein the region detection unit detects the region based on correspondence between information on a shape of the region of the examinee and the image information.

22. The information processing apparatus according to claim 19, further comprising a database that records information on relative positions and relative postures between the probe and the examinee beforehand,
wherein the obtaining unit calculates an amount of control using information recorded in the database.

23. The information processing apparatus according to claim 22, wherein the information recorded in the database indicates a state of the probe to make an ultrasonic image diagnosis.

24. The information processing apparatus according to claim 22, wherein the database records information on a pressure between the probe and the examinee.

25. The information processing apparatus according to claim 19, further comprising the probe, and
wherein the probe comprises a pressure measuring unit configured to measure a pressure between the probe and the examinee.

26. An information processing method for ultrasound imaging, the method comprising:
detecting a region to be medically inspected based on an image obtained from a probe;
detecting from an ultrasonic image another region different from the region to be medically inspected; and
obtaining information for moving the probe to the region to be medically inspected, based on one of: (a) a detection result obtained from the step of detecting the region to medically inspected and (b) both a detection result obtained from the step of detecting the other region different from the region to be medically inspected and stored information,
wherein the stored information is stored in a storage, and indicates a relative positional relationship between the region to be inspected and the other region.

27. A non-transitory computer-readable recording medium storing a computer program that causes a computer to execute the method according to claim 26.

28. A control apparatus imaging system including a probe for detecting, from an examinee, an acoustic wave for generating image data, the system comprising:
a region detection unit configured to detect a target region to be medically inspected;
a measuring unit configured to measure a relative position of the probe with respect to the examinee, based on a detection result from the region detection unit;
a control amount calculation unit configured to calculate an amount of control of the position of the probe, based on a measurement by the measuring unit and the detected target region; and
a display control unit configured to control a display unit to display image data and information for guiding the probe to the target region superimposed on the image data, based on the amount of control calculated by the control amount calculation unit.

* * * * *